US007053067B2

(12) United States Patent
Kuo et al.

(10) Patent No.: US 7,053,067 B2
(45) Date of Patent: May 30, 2006

(54) *CHLAMYDIA* OLIGOSACCHARIDES

(75) Inventors: Cho-chou Kuo, Seattle, WA (US); Albertina F. Swanson, Tucson, AZ (US); Sen-Itiroh Hakomori, Seattle, WA (US); Noriko Takahashi, Nagoya (JP)

(73) Assignee: The University of Washington, Seattle, WA (US)

( * ) Notice: Subject to any disclaimer, the term of this patent is extended or adjusted under 35 U.S.C. 154(b) by 0 days.

(21) Appl. No.: 10/732,281

(22) Filed: Dec. 11, 2003

(65) Prior Publication Data

US 2004/0138173 A1 Jul. 15, 2004

Related U.S. Application Data

(63) Continuation of application No. 10/287,587, filed on Nov. 5, 2002, now abandoned, which is a continuation of application No. 09/230,346, filed as application No. PCT/US97/13037 on Jul. 25, 1997, now abandoned, which is a continuation-in-part of application No. 08/672,849, filed on Jul. 25, 1996, now abandoned.

(51) Int. Cl.
*A61K 31/715* (2006.01)

(52) U.S. Cl. ............................................ 514/54; 514/8
(58) Field of Classification Search .................... 514/8, 514/54

See application file for complete search history.

(56) References Cited

U.S. PATENT DOCUMENTS 5,132,413 A 7/1992 Aizawa et al.

FOREIGN PATENT DOCUMENTS

EP 0 677 295 A1 10/1995

WO WO 93/05803 A1 1/1993
WO WO 95/11704 A1 4/1995

OTHER PUBLICATIONS

Swanson, et al., "Identification of Lectin-binding Proteins in *Chlamydia* Species", *Infection and Immunity*, Feb., 1990, vol. 58, No. 2, pp. 502-507.
Swanson, et al., "Binding of the Glycan of the Major Outer Membrane Protein of *Chlamydia trachomatis* to HeLa Cells", *Infection and Immunity*, Jan., 1994, vol. 62, No. 1, pp. 24-28.
Kuo, et al., "An N-linked High-mannose Type Oligosaccharide, Expressed at the Major Outer Membrane Protein Of *Chlamydia trachomatis*, Mediates Attachment and Infectivity of the Microorganism to HeLA Cells", *J. Clinical Investigation*, Dec., 1996, vol. 98, No. 12, pp. 2813-2818.
Kuo, et al., "Mannose-receptor Positive and Negative Mouse Macrophages Differ in their Susceptibility to Infection by *Chlamydia* Species", *Microbial Pathogenesis*, 2002, vol. 32, pp. 43-48.
Cho-chou Kuo, et al. "Cleavage of the N-Linked Oligosaccharide from the Surfaces of *Chlamydia* Species Affects Attachment and Infectivity of the Organisms in Human Epithelial and Endothelial Cells", Infection and Immunity, Nov. 2004, vol. 72, No. 11, pp. 6699-6701.
Cho-Chou Kuo, et al. "Infectivity of *Chlamydia* Pneumoniae and *Chlamydia trachomatis* is Abolished by N-Glycanase Treatment", Department of Pathobiology, University of Washington, Seattle, WA USA; Proceedings, Fifth Meeting of the European Society for *Chlamydia* Research, Budapest, Hungary, Sep. 1-4, 2004. (Editor Judith Deak) University of Szeged.
Noboru Tomiya, et al. "Analyses of N-Linked Oligosaccharides Using a Two-Dimensional Mapping Technique", Analytical Biochemistry, vol.: 171, pp. 73-90 (1988).

*Primary Examiner*—Leigh C. Maier
(74) *Attorney, Agent, or Firm*—Sughrue Mion, PLLC

(57) ABSTRACT

Oligosaccharides specific for *Chlamydia* mediate attachment of the organism to host

CHLAMYDIA OLIGOSACCHARIDES

This is a Continuation of application Ser. No. 10/287,587 filed Nov. 5, 2002, now abandoned which is a Continuation of S. application Ser. No. 09/230,346 filed Feb. 19, 1999 (abandoned), which is a 371 of PCT/US97/13037 filed Jul. 25, 1997, which is a continuation-in-part of U.S. application Ser. No. 08/672,849 filed Jul. 25, 1996 (abandoned).

Portions of the research described herein were supported in part by monies for the National Institutes of Health.

BACKGROUND OF THE INVENTION

*Chlamydia trachomatis* is one of the most common causes of blindness and sexually transmitted diseases in humans. *C. trachomatis* is an obligate intracellular bacterium which is biphasic. The intracellular form is the metabolically active reticulate body and the extracellular form is the infectious elementary body (EB) (Moulder et al. (1984) in *Bergey's Manual of Systemic Bacteriology* (Krieg, ed.) 1:729–735, Williams & Wilkins, Baltimore).

A prominently exposed component on the surface of the chlamydial EB involved in the initial interaction between *C. trachomatis* and the host cell is the major outer membrane protein (MOMP; Mr 40,000) (Caldwell & Judd (1982) *Infect. Immun.* 38:960–968). The MOMP is the principal structural protein of the EB and individual MOMP proteins are cross-linked by disulfide bonds to provide rigidity to the cell wall (Newhall & Jones (1983) *J. Bacteriol.* 154:998–1001). The serologic specificity of the organism resides in the MOMP and antibodies raised to MOMP can neutralize infectivity of chlamydia (Caldwell & Perry (1982) *Infect. Immun.* 38:745–754; Lucero & Kuo (1985) *Infect. Immun.* 50:595–597).

MOMP and two other chlamydial proteins (Mr 32,000 and 18,000) were identified as glycoproteins when the organisms were probed with various plant lectins (Swanson & Kuo (1990) *Infect. Immun.* 58:502–507). Further characterization showed the three proteins to be glycosylated by way of N-linkage, a structure means rarely found in bacteria (Wieland (1988) *Biochimie,* 70:1493–1504).

SUMMARY OF THE INVENTION

The carbohydrate moieties of the MOMP which are involved in the attachment of *C. trachomatis* and other chlamydiae to host mammalian cells can be used to block attachment and infectivity of chlamydiae.

Thus, among the objects of the instant invention are the identification of the relevant carbohydrates which mediate the binding of various chlamydiae to mammalian cells, which mediate the infectivity of various chlamydiae in mammalian cells, compositions comprising same and methods for using same to block binding of and infectivity of chlamydiae in a host.

Those and other objects of the instant invention have been attained by the discovery of novel N-linked structures in *chlamydia* MOMP, found to be of a "high mannose-type" which mediate binding of chlamydiae to mammalian host cells. Thus, the instant invention includes compositions and methods for precluding attachment of chlamydiae to host cells.

Inhibitory effects of glycopeptides were assayed by inclusion counts with fluorescent antibody staining of 3 day cultures. Strains tested were *Chlamydia trachomatis* $L_2$/434/Bu, *Chlamydia pneumoniae* AR-39 and *Chlamydia psittaci* 6BC. Each point is the average of 2 experiments. Positive and negative controls using neutralizing and non-neutralizing monoclonal antibodies reacted appropriately (data not shown). A reduction of more than 50% of inclusion counts in comparison to cultures inoculated with organism alone is regarded as positive neutralization of *chlamydia*. (Byrne et al. (1993) *J. Infect. Dis.* 168:415–420.)

Figure 2A:
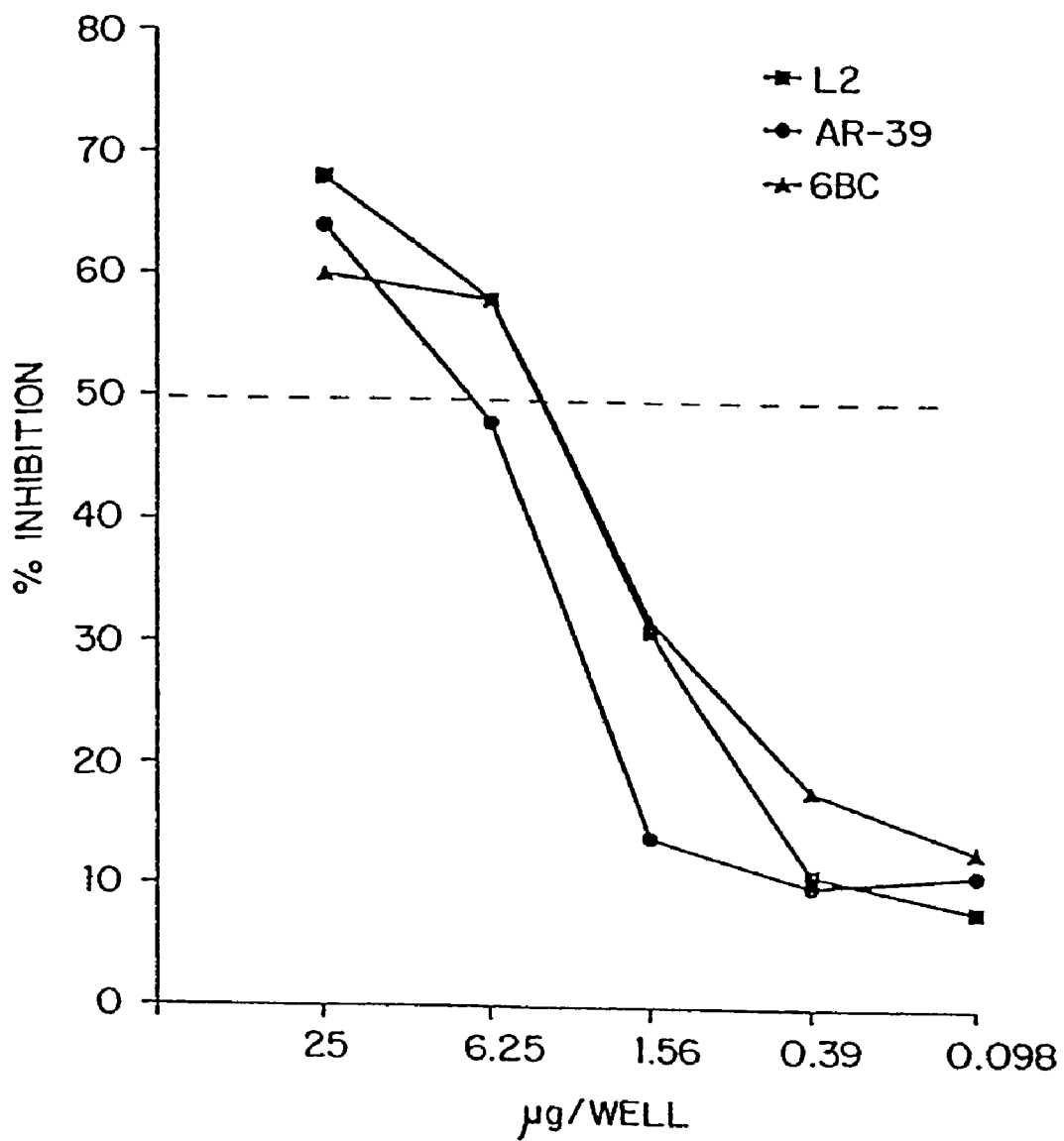
FIGS. 2A and 2B depict inhibition of infectivity of *Chlamydia* species in HeLa cells with glycopeptides from hen ovalbumin. Ovomucoid was fractionated into "high mannose-type" (FIG. 2A) and "complex-type" (FIG. 2B) glycopeptides using a ConA column. A four-fold dilution of glycopeptides was mixed with an organism suspension, incubated at 35° C. for 30 min. and inoculated onto HeLa cell monolayers, in duplicate.
Figure 2B:
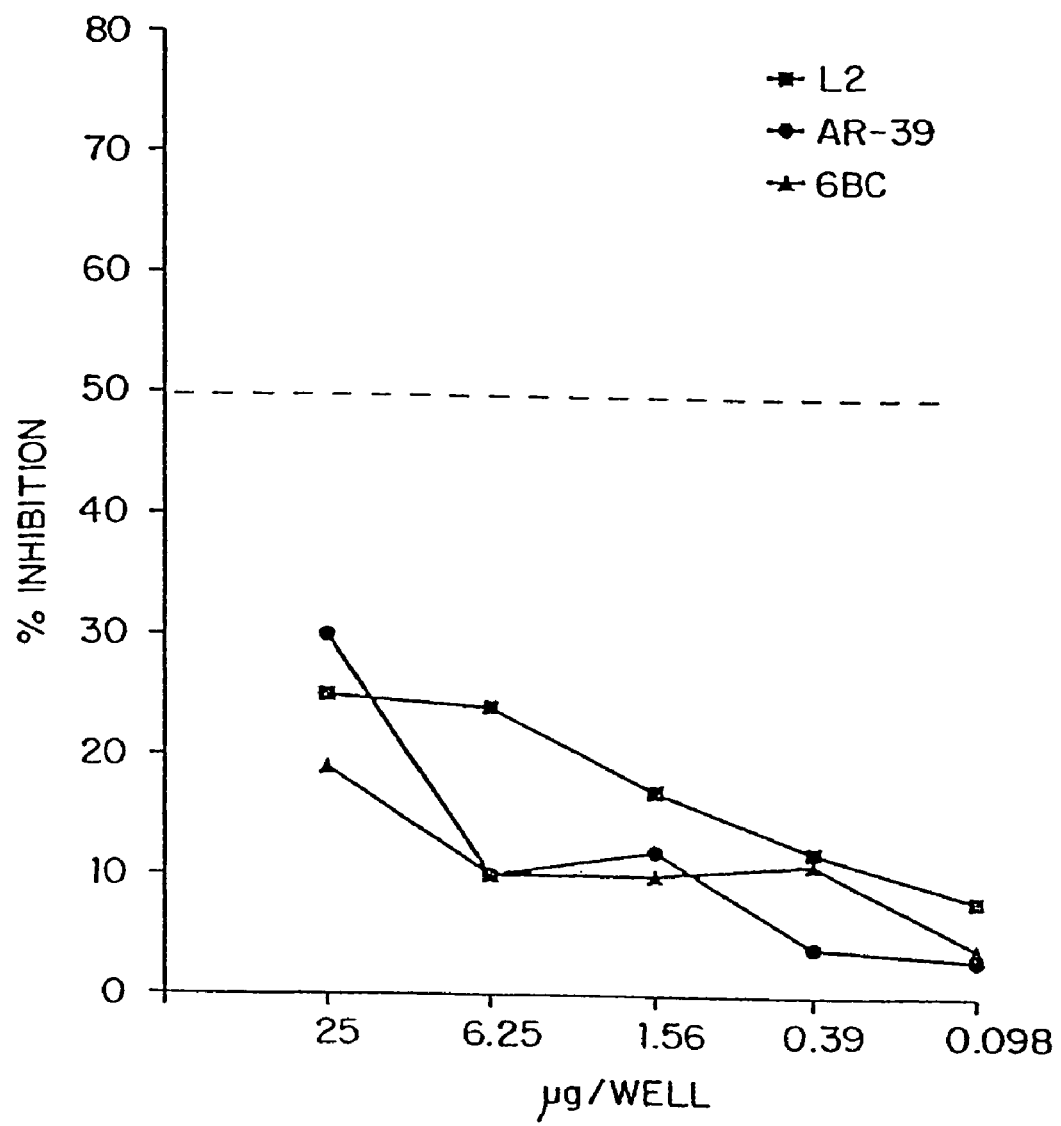
Figure 3A:
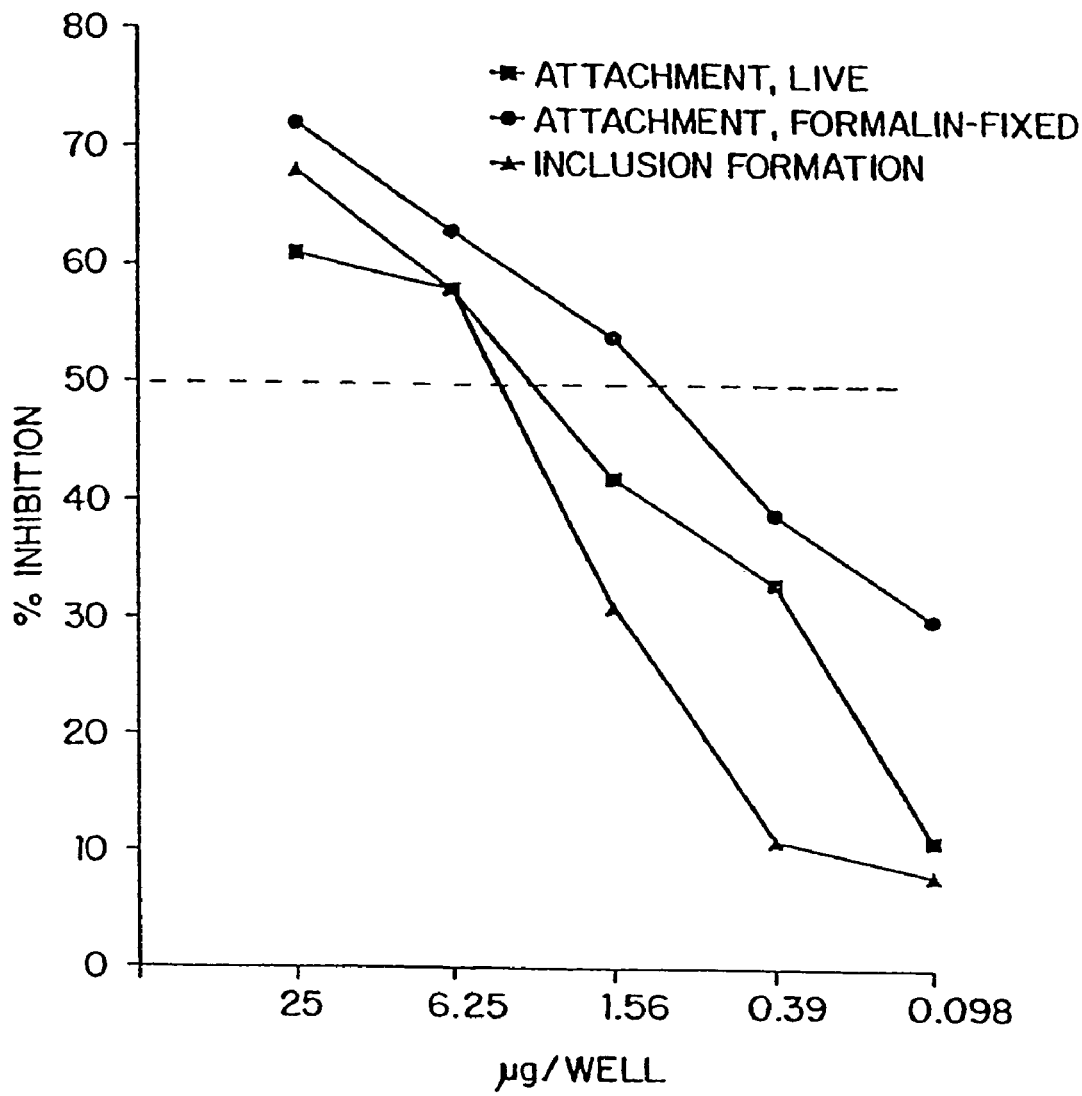
Figure 3B:
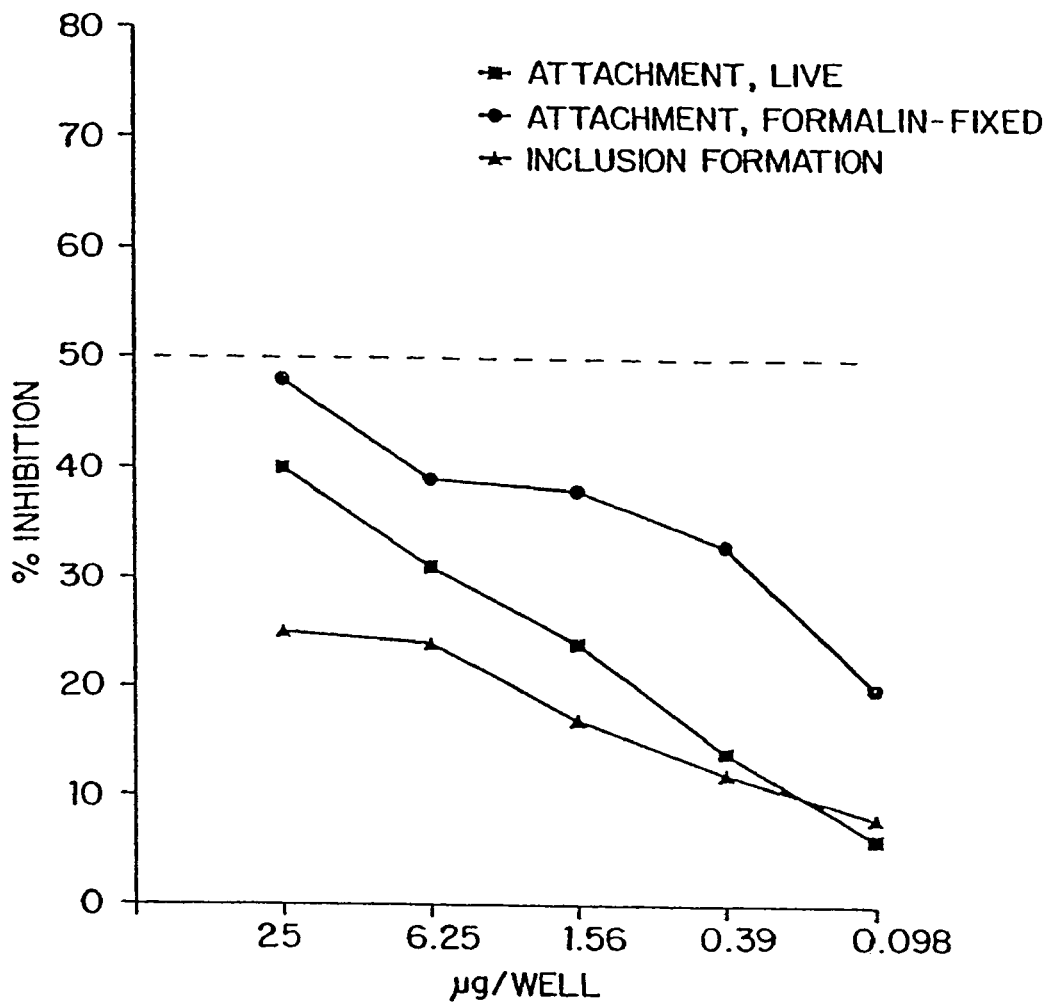

FIGS. 3A and 3B depict inhibition of attachment of *Chlamydia trachomatis* $L_2$/434/Bu to HeLa cells with glycopeptides from hen ovalbumin. Experiments using "high mannose-type" glycopeptides are shown in FIG. 3A and with complex glycopeptides in FIG. 3B. Tritium-labeled organisms, either live or formalin-fixed, were mixed with 4-fold dilutions of glycopeptides, incubated at room temperature for 30 min., inoculated onto HeLa cell monolayers in duplicate and absorbed at 4° C. for 30 min. Inocula were removed, cell monolayers washed and the radioactivity associated with cells counted. Each data point is an average of 2 experiments. Also shown for comparison are the inclusion counts in experiments depicted in FIGS. 2A and 2B.

DETAILED DESCRIPTION OF THE INVENTION

The carbohydrate moiety of the 40 kDa MOMP and other glycoproteins expressed on *chlamydia* are involved in attachment of the organism to host cells and the infectivity thereof, that is, the MOMP glycoprotein plays an essential role in the infectivity of the organism in mammalian cells. The carbohydrate moiety of the MOMP glycoprotein is recognized by host mammalian cells in the process of attachment and entry of the organism into host cells.

Mammalian cell proteins, particularly those at the cell surface membrane, often are N-glycosylated, that is, the amino group of asparagine (AsN) in the sequence, . . . ASN-X-Ser/Thr . . . , wherein X is an amino acid, is glycosylated through a stable N-glycoside linkage, as demonstrated in Table 1.

There are three types of relevant glycan structures: "high mannose-type", "complex-type" and "hybrid-type" (Kornfeld & Kornfeld (1980), "Structure of glycoproteins and their oligosaccharide units," in Lennarz, ed., *The Biochemistry Of Glycogroteins And Proteoglycans*, Plenum Press, New York). Those structures are considered essentially to be absent in bacteria, with a few rare exceptions (Wieland, supra). Nothing is known concerning the presence of such structures in chlamydiae, despite the fact that the carbohydrate moiety of MOMP is essential for determining and defining infectivity.

TABLE 1
Three basic types of N-linked glycans:
"high mannose-type", "complex-type", and "hybrid-type"
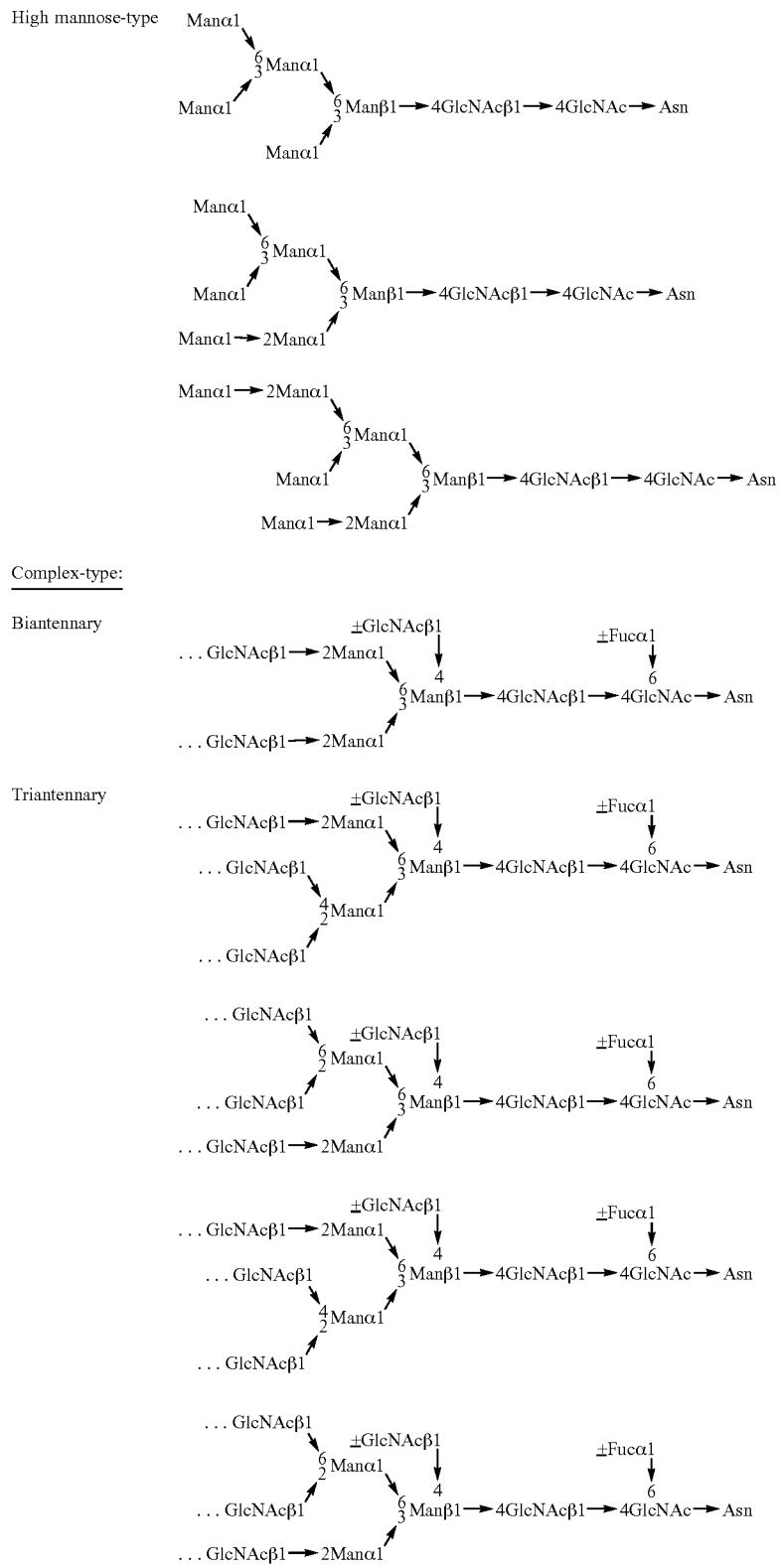

TABLE 1-continued

Three basic types of N-linked glycans:
"high mannose-type", "complex-type", and "hybrid-type"

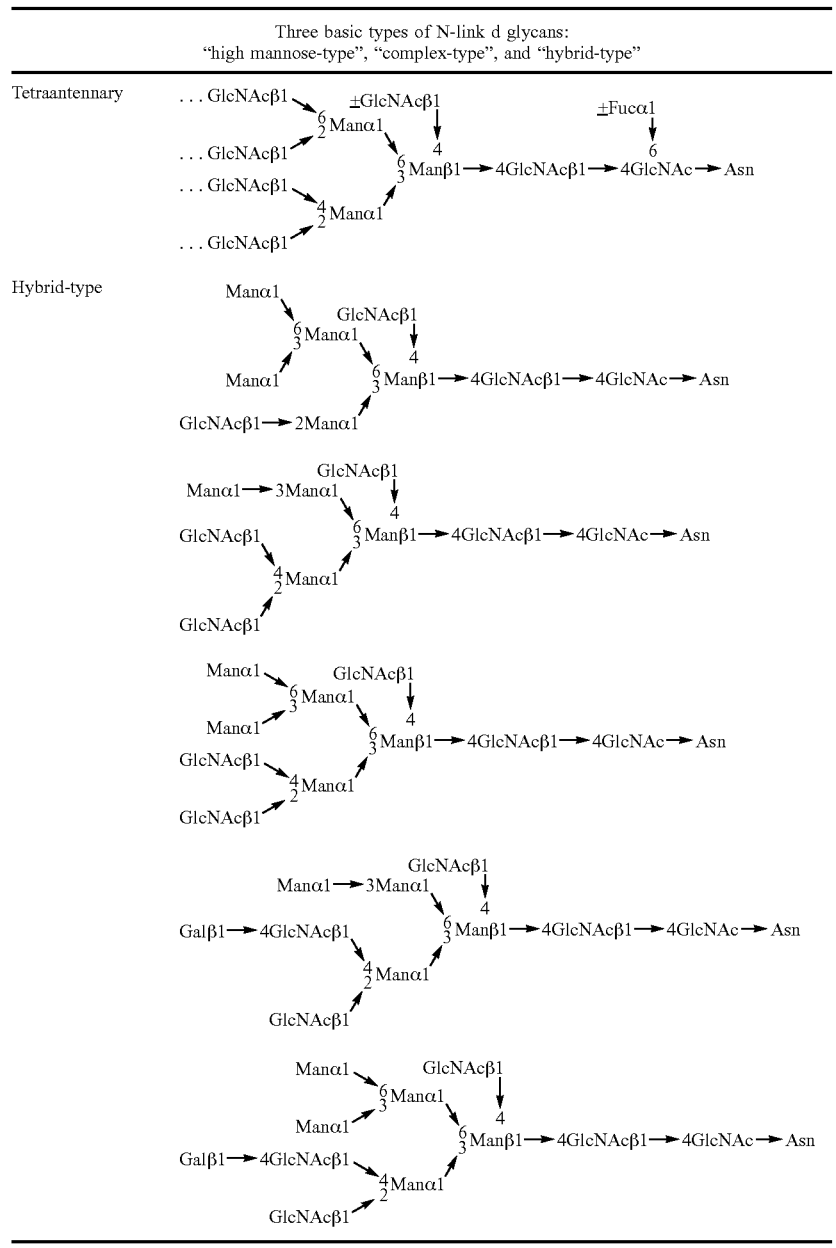

The carbohydrate moiety of MOMP binds ConA, wheat germ agglutinin (WGA) and *Dolichos biflorus* agglutinin; but does not bind to lectins from *Ulex europaeus* agglutinin, soybean agglutinin or *Ricinus communis* agglutinin. Thus, it appears that N-acetyl galactosamine (GalNAc), galactose (Gal) or fucose (Fuc) is not present or not exposed on MOMP.

Binding to WGA is not affected by sialic acid in a hapten inhibition assay or by treatment with sialidase indicating in the *chlamydia* carbohydrate sialic acid is not present or not exposed on MOMP, but rather that WGA binding likely is attributable to N-acetyl glucosamine (GlcNAc).

The presence of an asparagine (Asn)-linked (N-linked) glycan structure in MOMP is suggested by the susceptibility thereof to endoglycosidase-F or to N-Glycanase™. The possible presence of a "high mannose-type" structure or a "complex-type" structure is suggested by the susceptibility to ∝-mannosidase and by binding thereof to WGA. The large quantity of mannose present in MOMP also indicates the presence of "high mannose-type" structure as a major component.

The "high mannose-type" structure may contribute to or mediate the attachment of *chlamydia* to a host cell, and could define infectivity, regardless of species (*C. trachomatis*, *C. pneumoniae*, or *C. psittaci*). That revelation is contrary to the generally accepted belief that N-linked structures essentially are absent in microorganisms. However, application of ultramicroanalysis techniques able to analyze a sample of less than 100 μg of glycan contributed, in part, to discarding that notion.

Relatively large quantities of glycopeptides containing "high mannose-type", "complex-type" or "hybrid-type"

structures from novel, analogous sources (e.g. ovalbumin) can be used to determine the inhibitory effects of glycopeptides on the infectivity of *chlamydia*.

Glycopeptides of the "high mannose-type" showed greater inhibition of infectivity of *chlamydia* species than those of the "complex-type" or "hybrid-type". The same trend was observed for inhibition of attachment of live and formalin-fixed organisms to mammalian cells. Of the "high-mannose-type" oligosaccharides, those having about 8 mannose (Man) residues showed stronger inhibitory effect than those having other numbers of residues.

Accordingly, carbohydrates containing high levels of terminal mannose residues are suited for blocking attachment of *chlamydia* to mammalian cells. Ovalbumin is found to be a practical source of oligosaccharides containing high levels of terminal mannose residues. Hence, ovalbumin can serve as a suitable source of carbohydrates in the practice of the instant invention. However, ovalbumin sugars can be smaller than *chlamydia* sugars, particularly of the "high mannose-type". Additional mannose residues can be added to the one, two or three branches of the ovalbumin oligosaccharides using known techniques to simulate the oligosaccharides of *chlamydia*.

The presence of N-linked structures in MOMP glycoprotein of *chlamydia* was indicated by the susceptibility thereof to N-glycanase, which causes release of all oligosaccharides. The released oligosaccharides were fluorescence-labeled by pyridylamination followed by two-dimensional HPLC with ion-exchange and hydrophobic chromatography to distinguish the molecules.

None of the oligosaccharides released from MOMP glycoprotein were sialylated. Many of the species separated (see the peaks identified as A, B, C, D and F in FIG. 1) were of the "high mannose-type". Other species of interest, such as those peaks identified as G and I of FIG. 1, were of the "complex-type".

A common carbohydrate structure with an inhibitory effect on infectivity of chlamydia organisms is one of the "high mannose-type". That structure is defined by the presence of: (i) a trimannosyl core; (ii) mannosyl substitution or branching at an ∝1→6Man residue of the trimannosyl core; and (iii) mannosyl substitution or branching at an ∝1→3Man residue of the trimannosyl core.

The trimannosyl core, consisting of two mannosyl branches linked ∝1→6 and ∝1→3, respectively, to a mannose residue, is linked to a β-GlcNAc residue of a chitobiosyl structure (GlcNAcβ1→4GlcNAc) linked to AsN, is a common feature of N-linked structures, i.e. "high mannose-type", "complex-type" and "hybrid-type" structures. The "high mannose-type" structure is characterized by multiple ∝-mannosyl substitutions or branching at the trimannosyl core as described above.

More particularly, a "high mannose-type" structure of interest is one with about 8 or more mannose residues. For example, structures wherein the mannose residues linked to the ∝1→6Man and ∝1→3Man branches of the trimannosyl core are of the ∝1→6Man, α1→2 and ∝1→3Man linkage forms in combination with optional ∝1→2Man substitution at nonreducing Man residues, such as those containing about 10 or 11 mannose residues (identified as Man10 in Table 2, class 1) are of interest.

TABLE 2

"High mannose-type" structures that inhibit chlamydia infectivity.

Class 1

Man10

Manα2Manα\
　　　　　　＞₃⁶Manα\
(±Manα2)Manα／　　　　　＞₃⁶Manβ4GlcNAcβ4GlcNAc
Manα2Manα2＼Manα／
Manα2Manα6／

Class 2

Man8 and Man9

Manα2Manα＼
　　　　　　＞₃⁶Manα＼
(±Manα2)Manα／　　　　　＞₃⁶Manβ4GlcNAcβ4GlcNAc
Manα2Manα2Manα／

Class 3

Man6 and Man7

Manα＼
　　　＞₃⁶Manα＼
Manα／　　　＞₃⁶Manβ4GlcNAcβ4GlcNAc
(±Manα2)Manα2Manα／

Class 4

Man6b and Man7b (±Manα2)Manα＼
　　　　　　　＞₃⁶Manα＼
Manα／　　　　＞₃⁶Manβ4GlcNAcβ4GlcNAc
(±Manα2)Manα／

Alternatively, certain structures of interest have a second ∝1→6Man and ∝1→3Man branch at the α1→6Man branch of the trimannosyl core, in combination with optional ∝1→2Man substitution at the non-reducing ends, and with α1→2 substitution at the α1→3 branch of the trimannosyl core, such as the Man8 and Man9 structures of Table 2, class 2.

Other structures of interest are those with a second ∝1→6Man and ∝1→3Man branch at the ∝1→6Man branch of the trimannosyl core but without α1→2 substitution thereof, and ∝1→2Man substitution at the ∝1→3Man branch of the trimannosyl core, such as Man6 and Man7 depicted in Table 2, class 3.

The same structure as Man8 or Man9 but with optional peripheral ∝1→2Man substitutions can result in structures such as Man6b or Man7b depicted in Table 2, class 4.

Those four classes of "high mannose-type" oligosaccharides inhibited *chlamydia* adhesion and entry into host mammalian cells, for example, as observed in experiments with HeLa cells. In some experiments, Man8 showed the strongest inhibition, followed by Man9, Man7 and Man6. A mixture of Man7b and Man6b prepared from ovalbumin glycopeptide had an inhibitory effect comparable to that of Man9, Man7 and Man6.

Certain "complex-type" or "hybrid-type" oligosaccharides showed a lesser inhibitory effect.

Various "high mannose-type" structures which are N-linked to MOMP expressed at the surface of chlamydiae are of particular interest because of the role of such in defining infectivity of the organism.

Thus, a carbohydrate of interest is one containing plural mannose residues at the terminus of a linear carbohydrate backbone wherein the terminal residue of the backbone to which a mannose is bound is an N-acetyl glucosamine (GlcNAc) residue.

Generally, a plurality of mannose residues in a linear and branch form are present. Generally, about five mannose resides are present, see for example Man6b and Man 7b. Optional α1→2 substation can be present at the reducing ends increasing the mannose count.

A terminal mannose can serve as a branch point to which two mannose residues bind resulting in a bifurcated or bi-antennary molecule. Mannose residues then can form two linear chains from that branch point. Either branch itself can bifurcate resulting in a trifurcated or tri-antenarry molecule, or a tetra-antenarry molecule.

Preferred structures are those of the "high mannose-type" having at least five mannose residues and up through 12 or more mannose residues. Those containing 6, 7, 8, 9, 10, 11 or 12 residues are of particular interest. A preferred structure also is tri-antennary, that is, contains three branches. Also, a preferred structure has a mannose residue at the reducing ends.

The carbohydrates of the instant invention can be made using known techniques or from commercially available starting materials. The carbohydrates can be isolated from appropriate sources using known extraction techniques. Some of those methods are exemplified herein. Alternatively, the carbohydrates of interest can be synthesized chemically or enzymatically and reference to some of those techniques is made herein.

The carbohydrates of interest are found on a plurality of chlamydial species and thus may typify the genus, that is, *chlamydia* may share a common mechanism and means for binding to and infecting mammalian cells and the instant carbohydrates are useable on any of a variety of *chlamydia*.

The carbohydrates of interest can be used to intervene in the attachment and infectivity processes of chlamydial interaction with host mammalian cells and thus can serve a prophylactic or treatment role for combatting chlamydial infection.

*Chlamydia* are responsible for a variety of maladies. In human, *C. psittacosis* can cause fever and pneumonia. *C. pneumonia* is responsible for respiratory disorders, such as, pneumonia, bronchitis and sinusitis, and more recently has been correlated with the development of atherosclerotic plaques. Thus, the presence of *chlamydia* has been correlated with coronary heart disease, myocarditis and endocarditis.

*C. trachomatis* is associated with vision disturbances and blindness as well as with sexually transmitted disease. The organism can affect a variety of reproductive organs. Chlamydial infections can be more severe in the female resulting ultimately in infertility or ectopic pregnancy.

Current therapy of chlamydial infection relies primarily on known antibiotic treatment means. However, antibiotic therapy often fails to cure the infection because the organism resides and proliferates intracellularly. Thus, antibiotic therapy may be only partially effective, and particularly only in the early stages of infection.

Because the carbohydrates of the instant invention block attachment of *chlamydia* to mammalian cells, the instant carbohydrates can be used to retard the transmission and dissemination of disease as well as prohibit progression of an infection. The instant carbohydrates can be used in conjunction with standard antibiotic therapy, by blocking attachment and rendering the organisms more susceptible to the known actions of the antibiotics.

The instant carbohydrates can be modified to enhance desirable characteristics thereof. For example, various residues can be substituted by analogs to obtain desirable characteristics, such as to prolong the half-life of the molecule thereby enhancing the stability of the molecule in circulation.

Also, because the branching structure and terminal mannose residues appear to play a key role in the recognition and infectivity processes, artificial carbohydrates containing greater than three branches can be configured, using known biosynthetic or chemical synthetic methods, for example, see Merritt et al. (1994) *J. Org. Chem.* 59:4443–4449.

Those branched structures also can contain mannose residues or structurally similar replacements therefor which provide the same function as a mannose residue but which have ancillary beneficial properties, such as resistance to certain enzymes which, for example, might catalyze the removal of terminal mannose residues from a carbohydrate.

The specific choice of starting materials to construct an analog molecule which can substitute for a naturally occurring "high mannose-type" molecule of interest but which contains one or more replacements of residues to obtain a molecule with enhanced binding or other beneficial features, such as prolonged half-life, can be made in view of known molecules and mimics which can substitute, for example, for mannose. A means for determining whether an analog or derivative is useable is whether the resulting analog or derivative continues to inhibit attachment of a *chlamydia* to a host cell, using for example, a binding assay as taught herein.

For example, some of those key features of the carbohydrates of interest can be reproduced by mimetics generated by computer assisted rational drug design methods. Thus, the spatial and electronic configuration of the key structural features of a carbohydrate of interest can be produced using more stable components, which need not be saccharides.

Also, a suitable oligosaccharide e.g. Man8 or Man9, can be assembled in multivalent form by linking one or more of such molecules to a scaffold carrier molecule, thus providing a plurality of "high mannose-type" structures on a single molecule using methods known in the art. Such multivalent "high mannose-type" structures are likely to have a greater effect on inhibiting binding of *chlamydia* organisms to host cells.

Carbohydrates with an initial lower inhibiting activity can find beneficial use if made multivalent, i.e. linked to a common carrier with suitable spacing. The carrier can be any known inert molecule to which the carbohydrates of interest can be bound using known chemistries. The carrier can be a synthetic molecule or an isolated naturally occurring molecule.

Such bivalent or multivalent binding sites could demonstrate an enhanced avidity for a ligand and thus inhibit binding much more efficiently. That concept is termed "monogamous multivalency" (Klinman & Karush (1967). *Immunochemistry* 4: 387–390). A monogamous multivalent structure, relative to a single site, is favored to bind to the ligand by a factor of $10$ or $10^4$ (Hormick & Karush (1972) *Immunochemistry* 9: 325–328).

The instant invention therefor provides pharmaceutic compositions and methods for treating disorders normally associated with chlamydial infection, such as, optic disor ders, respiratory disorders and reproductive disorders comprising:

(1) an amount of an oligosaccharide, or pharmaceutically acceptable salts thereof sufficient to inhibit attachment of *chlamydia* to mammalian cells, and (2) a pharmaceutically acceptable carrier, diluent or excipient.

A suitable oligosaccharide is one with a branched terminus comprising a plurality of mannose residues which can block the attachment of *chlamydia* to mammalian cells.

The compositions and methods are applicable both for in vitro and in vivo applications. For example, the instant oligosaccharides can be included in tissue culture medium for use with fastidious or valuable cells and cultures as a means for avoiding contamination or loss. Specific other uses include treatment of disorders and disease states arising from chlamydial infection.

The composition comprises an effective amount of an appropriate oligosaccharide and a pharmaceutically acceptable carrier, diluent or excipient. The effective amount of an oligosaccharide can be determined using art-recognized methods, such as by establishing dose-response relationships in suitable animal models or in non-human primates and extrapolating to human; extrapolating from suitable in vitro data, for example, as described herein; or by determining effectiveness empirically in clinical trials.

Suitable doses of a composition of the instant invention depend on the particular medical application, such as the severity of the disease, the weight of the subject, age of the subject, the half-life in circulation etc., and can be determined readily by the skilled artisan practicing known techniques. The number of doses, daily dosage and course of treatment may vary from subject to subject.

Generally the effective doses are derived or extrapolated from in vitro studies as done for antibiotics (Kuo et al. (1977) *Antimicrob. Agents Chemotherapy,* 12:80–83; Kuo et al. (1988) *Antimicrob. Agents Chemotherapy,* 32:257–258). For example, defined oligosaccharides showed inhibitory effects of infectivity at 20 μg (Table 4), while glycopeptides of egg albumin were shown to inhibit infectivity and attachment at concentrations of 6.25 μg and 1 μg (FIG. 2A and FIG. 3A). Thus, synthetic oligosaccharides may be tested for their inhibitory activities by such known methods.

As is known in the pharmaceutic arts, the kinetics of achieving an appropriate and effective blood concentration depend, for example, on the route of administration, serum molecules which sequester the instant compounds, enzymes that inactivate the instant compounds and the like. But the pharmacokinetics of the instant compounds can be determined following art-recognized methods, such as, administering radiolabelled compound to a test subject and following the time course of plasma presence, tissue distribution and the like.

Hence, the dose of the instant compounds administered intravenously and the number of doses are determinable by such kinetic data and generally would be adjusted to higher concentrations for an oral or topical form.

The oligosaccharides can be administered in a variety of ways such as orally, parenterally and topically. Suitable pharmaceutically acceptable carriers, diluents or excipients for the medicaments of the instant invention depend on the particular use of the medicament and can be determined readily by the skilled artisan. Also, the oligosaccharides can be delivered encapsulated within microspheres, such as liposomes, which can be made of, for example, phosphatidylcholine and cholesterol.

The medicament can take a variety of forms, such as, tablets, capsules, bulk or unit dose powders or granules; may be contained within liposomes; or may be formulated into solutions, emulsions, drops, suspensions, ointments, pastes, creams, gels, foams or jellies. Parenteral dosage forms include solutions, suspensions and the like. The medicament is likely to contain any of a variety of art-recognized excipients, diluents, fillers etc. Such subsidiary ingredients include disintegrants, binders, lubricants, surfactants, emulsifiers, buffers, moisturizers, solubilizers and preservatives. The artisan can configure the appropriate formulation comprising the oligosaccharides of interest seeking guidance from numerous authorities and references such as, *Goodman & Gilman's. The Pharmaceutical Basis of Therapeutics* (6th ed., Goodman et al., eds., MacMillan Publ. Co., NY, 1980).

Generally, the effective doses are derived or extrapolated from in vitro studies. As is known in the pharmaceutic arts, the kinetics of achieving an appropriate and effective blood concentration depend, for example, on the route of administration, serum molecules which sequester the instant compounds, enzymes that inactivate the instant compounds and the like. But the pharmacokinetics of the instant compounds can be determined following art-recognized methods, such as, administering radiolabelled compound to a test subject and following the time course of plasma presence, tissue distribution and the like.

A suitable form of administration is oral, but generally higher concentrations are required as are modifications which would render the instant compounds resistant to the effects of the gastro-intestinal tract. Alternatively, the instant compounds can be contained within microcapsules, such as liposomes, for enhanced delivery.

For respiratory indications, an aerator means of delivery may be preferred, although an oral or parenteral means is possible as well.

In optic indications, the instant carbohydrate may be instilled as drops or as an ointment.

In reproductive applications, the instant carbohydrate may be delivered by a topical means, such as, a liquid, suppository, foam or gel. Other gynecologic application means, such as impregnation in a porous, inert support, such as a sponge, can be used.

Hence, the biologically effective amount is that amount which yields an observable beneficial change from an abnormal state. The change can be curtailment or stoppage of disease progression or prophylaxis. The determination of a suitable dose thus depends on the abnormal state and is obtained by an artisan practicing known methods, generally an empirical assessment built on cumulative animal and clinical studies. Determination of dose is not a critical aspect of the instant invention.

Because of the relatedness of the instant compounds, a plurality of species can be used in place of one species. The amounts of each species initially is that amount which additively would yield the aggregate amount disclosed herein. However, lower doses of some or all of the species in a combination may be used.

In body sites that are relatively inaccessible, oligosaccharides can be administered in a suitable fashion to assure effective local concentrations. For example, oligosaccharides may be injected in a depot or adjuvant, carried in a surgically situated implant or reservoir that slowly releases a fixed amount of oligosaccharides over a period of time or may be complexed to recognition molecules with the capability of binding to the site presenting with abnormality. An example of such a contemplated scenario is a recognition molecule that is an antibody.

The instant invention now will be exemplified in the following non-limiting examples.

EXAMPLE 1

Hypaque-76 was obtained from Winthrop Laboratories, Sterling Drug Inc., New York, N.Y. Structurally defined oligosaccharides were obtained from Oxford GlycoSystems, Rosedale, N.Y. N-glycanase was obtained from the Genzyme Corp., Boston, Mass. Hen egg ovalbumin and pronase B were obtained from Sigma, St. Louis, Mo. Concanavalin A (ConA)-Sepharose and Sephadex G-50 were from Pharmacia AB, Uppsala, Sweden. Tritiated leucine was from Du Pont NEN, Boston, Mass. NCS tissue solubilizer and aqueous counting scintillant were from Amersham, Arlington Heights, Ill.

Chlamydial strains used were *C. trachomatis* $L_2$/434/Bu, *C. pneumoniae* AR-39 and *C. psittaci* 6BC. The organisms were grown in HeLa 229 cells and purified by Hypaque gradient centrifugation (Kuo et al. (1977) in *Nongonococcal urethritis and related infections*, Hobson & Holmes, ed.), pp. 328–336, American Society for Microbiology, Washington, D.C.). Two hundred fifty mg of purified organisms from five hundred 112 $cm^2$ culture flasks were used for preparing membrane glycoprotein.

The membrane glycoproteins were prepared from *C. trachomatis* $L_2$/434/Bu as described previously (Swanson & Kuo (1994) *Infect. Immun.* 62:24–28). MOMP glycoprotein was separated from other proteins in a SDS-12.5% polyacrylamide gel. The 40 kDa band was excised, electroeluted from the gel and stored at −20° C. The material was pooled and concentrated by centrifugation at 5,000×g at 4° C. in an Ultrapure filter unit with an exclusion factor of 10,000 molecular weight (Millipore, Bedford, Mass.). The isolated glycoprotein was delipidated by methanol-chloroform fractionation according to Finne & Krusius (*Methods Enzymol.* (1982) 83:269–277). The glycan was released from the glycoprotein by incubating for 48 h at 37° C. with 0.2 U of N-glycanase. Boiling for 5 min. halted the enzyme reaction. Following the addition of 3 volumes of ice-cold 95% ethanol, the mixture was centrifuged at 5,000×g for 10 min. The supernatant was removed and saved. The pellet was washed with 75% ethanol and centrifuged again. The supernatants were combined and dried with a stream of nitrogen. The residue was used for structural analysis.

Determination of N-linked oligosaccharides was performed by the two-dimensional sugar mapping technique developed by Tomiya et al. (*Anal. Biochem.* (1988) 171: 73–90) and described by Takahashi & Tomiya (*Handbook of Endoglycosidases and Glycosamimidases*, Takahashi & Muramatsu, eds., pp. 183–332, CRC Press, Boca Raton, Fla.). In the procedure, the oligosaccharides released were first pyridylaminated in the presence of sodium cyanoborohydride and then subjected to sequential high pressure liquid chromatography (HPLC), first with a reverse phase octadecylsilyl (ODS)-silica column and then with an amide-silica column.

Assays of inhibition of cell culture infectivity by glycopeptides or oligosaccharides were performed using HeLa 229 cell monolayers grown in 96-well microtiter plates (Byrne et al., supra). Serial four-fold dilutions of glycoconjugates were made. Ninety μl of each glycoconjugate dilution and 2×10$^{-4}$ inclusion forming units/ml of organism suspensions were mixed in a microtiter well and incubated at 35° C. for 30 min. Fifty μl of glycoconjugate/organism mixture were inoculated onto HeLa cell monolayers in duplicate and absorbed at 35° C. for 2 h on a rocker platform. Inocula then were removed and the monolayers were washed with Hanks' balanced salt solution. Culture medium was added to the wells, the plates were sealed with parafilm and incubated at 35° C. for 72 h.

Infectivity was assayed by counting inclusions that were stained by immunofluorescence using a fluorescein isothiocyanate-conjugated chlamydia genus-specific monoclonal antibody, such as, CF-2. Positive controls included monoclonal antibodies 155-35 and RR-402 which neutralize infectivity of $L_2$ and AR-39, respectively. Monoclonal antibody KK-12 which does not have neutralizing activity was used as a negative control. The monoclonal antibodies have been described previously (Lucero & Kuo (1985) *Infect. Immun.* 50:595–597; Swanson & Kuo (1994) *Infect. Immun.* 62:24–28; and Puolakkainen et al. (1995) *Microbiol. Immunol.* 39:551–554). A reduction of more than 50% of inclusion counts is regarded as indicating positive neutralization of *chlamydia* (Byrne et al. supra).

Chlamydial organisms were labeled metabolically by culturing with low leucine (1/10 of the normal concentration)-Eagle's minimum essential medium containing 50 μCi of [$^3$H]-leucine per 112 $cm^2$ flask in the presence of 0.8 ug/ml cycloheximide (Kuo & Grayston, J. T. (1976) *Infect. Immun.* 13:1103–1109). Tritium-labeled organisms were purified by centrifugation through a cushion of 30% Hypaque-76 and resuspended in phosphate buffered saline (PBS). An aliquot was used for preparation of formalin-fixed organisms by addition of 0.02% formalin (final concentration) and incubation at 4° C. for 72 h. Formalin was removed by centrifugation and a wash with PBS.

Inhibition of attachment of tritiated chlamydial organisms to HeLa cell monolayers grown in culture vials was assayed as described previously (Kuo & Grayston (1976) *Infect. Immun.* 13:1103–1109). Both live and formalin-fixed organisms were tested. Serial four-fold dilutions of glycopeptides were mixed with organisms and incubated at room temperature for 30 min. Glycopeptide/organism mixtures were inoculated onto HeLa cell monolayers in duplicate and incubated at 4° C. for 30 min. Inocula were removed and cell monolayers were washed 3 times with PBS. One ml of tissue solubilizer was added per vial and incubated at room temperature overnight. The digested tissue suspension was dissolved in 10 ml of scintillation fluid and the radioactivity counted in a scintillation counter (LS-5800 series, Liquid Scintillation System, Beckman Instrument, Inc., Palo Alto, Calif.).

Figure 1:
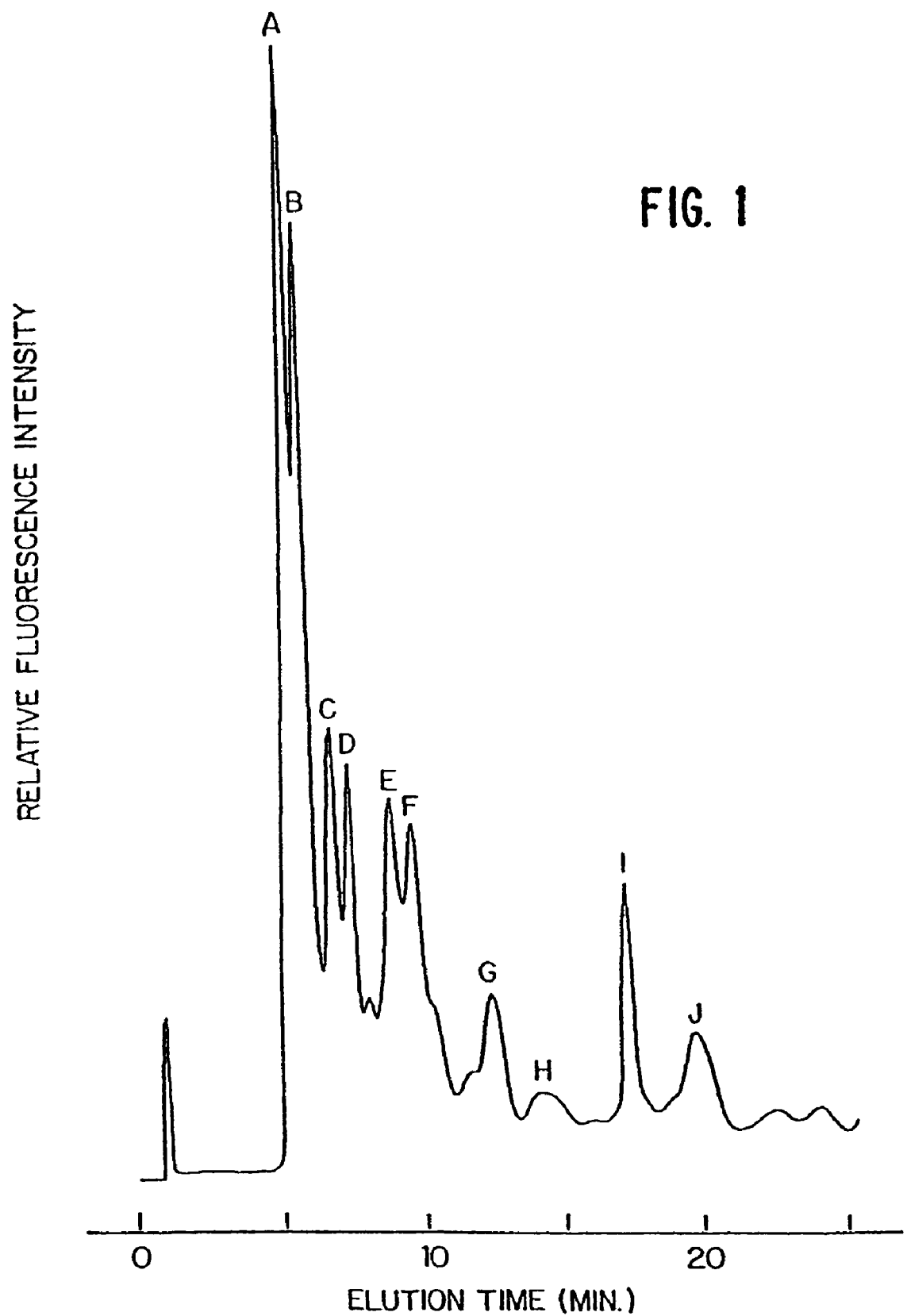
FIG. 1 depicts a chromatographic separation of pyridy-laminated oligosaccharides of the glycan from the 40-kDa MOMP glycoprotein. The structure of the oligosaccharide in each peak is provided in Table 3.

Ten fluorescent-labeled oligosaccharide peaks were separated by HPLC (peaks A to J in FIG. 1). Peaks A through F comprised about 80% of the total oligosaccharides. Peaks A through D and F were identified as "high mannose-type" by two-dimensional sugar mapping as summarized in Table 3. Peaks G and I were identified as a triantennary and biantennary oligosaccharides, respectively, that contained terminal galactose (Table 3). Quantities of some oligosaccharides were low, such as for peaks E, H and J. The oligosaccharides were N-linked. No sialic acid was found and no O-linked oligosaccharides were detected.

TABLE 3

N-Linked oligosaccharide structures of the 40-kDa glyoprotein of *Chlamydia trachomatis*.
The oligosaccharide structure of the corresponding peak from FIG. 1 is shown.

| Peak | Code no.[a] | Percent | Structures |
|---|---|---|---|
| A | M8.1 | 34.3 | Manα2Manα6\\Manα6\\ManP4GlcNAcP4GlcNAc / Manα3 / Manα2Manα2Manα3 |
| B | M9.1 | 21.7 | Manα2Manα6\\Manα6\\ManP4GlcNAcP4GlcNAc / Manα2Manα3 / Manα2Manα2Manα3 |
| C | M7.1 | 8.5 | Manα6\\Manα6\\ManP4GlcNAcP4GlcNAc / Manα3 / Manα2Manα2Manα3 |
| D | M6.1 | 7.3 | Manα6\\Manα6\\ManP4GlcNAcP4GlcNAc / Manα3 / Manα2Manα3 |
| F | M5.1 | 14.0 | Manα6\\Manα6\\ManP4GlcNAcP4GlcNAc / Manα3 / Manα3 |
| G | 300.18 | 5.9 | Galβ4GlcNAcβ6\\Manα6\\ManP4GlcNAcP4GlcNAc / Galβ4GlcNAcβ2 / Galβ4GlcNAcβ2Manα3 |
| I | 200.4 | 8.3 | Galβ4GlcNAcβ2Manα6\\ManP4GlcNAcP4GlcNAc / Galβ4GlcNAcβ2Manα3 |

[a]Standards based on unit contribution (Takahashi & Tomiya (1992) supra)

The infectivity-inhibitory effects of pure, defined "high mannose-type" oligosaccharides with different structures and different numbers of mannose residues were examined. The effects were compared to those of "complex-type" and "hybrid-type" oligosaccharides. All oligomers were tested at three concentrations, 20, 5 and 1 μg. The maximum inhibition was seen at 20 ug for each oligomer. Oligosaccharides of Man-8 (contains eight terminal mannose residues) (D1, D3), which has a structure similar to the oligosaccharide of peak A from MOMP (FIG. 1 and Table 3), demonstrated the strongest inhibitory effect on infectivity, followed by Man-9, then Man-6 and Man-7 in that order (Table 4), which had structures similar to the oligosaccharides of peaks B, D and C, respectively. The tri-antennary and bi-antennary structures corresponding to peaks G and I, respectively, had similar activity to Man-6 and Man-7; conserved trimannose core structure had minimal activity. Oligosaccharides not found in chlamydial glycan including an isomer of Man-8 and di-sialylated or galactosylated biantennary oligosaccharide also were tested. Only the "high mannose-type" oligosaccharides showed an inhibitory effect.

TABLE 4

Infectivity inhibition with oligosaccharides. Oligosaccharide analogs to those found in the glycoprotein of *Chlamydia trachomatis* were tested for their ability to inhibit infection of HeLa cells. Percent inhibition shows two separate sets of experiments at the maximum concentration (20 μg) tested.

| OLIGOSACCHARIDES | PEAK | % INHIBITION |
|---|---|---|
| oligomannose 9 | B | 64, 62 |
| oligomannose 8 D1, D3 | A | 74, 75 |
| oligomannose 8 (isomer) | (-)[b] | 55, 56 |
| oligomannose 7 D3 | C | 46, 49 |
| oligomannose 6 | D | 54, 54 |
| asialo-, galactosylated | G | 50, 46 |

TABLE 4-continued

Infectivity inhibition with oligosaccharides. Oligosaccharide analogs to those found in the glycoprotein of *Chlamydia trachomatis* were tested for their ability to inhibit infection of HeLa cells. Percent inhibition shows two separate sets of experiments at the maximum concentration (20 µg) tested.

| OLIGOSACCHARIDES | PEAK | % INHIBITION |
|---|---|---|
| triantennary asialo-, galactosylated | I | 45, 42 |
| biantennary d-sialylated-, galactosylated | (-) | 20, 34 |
| biantennary conserved trimannosyl core | (core)[c] | 26, 29 |

[a] See FIG. 1 and Table 1 for structures
[b] (-) sign indicates structures not found in chlamydia
[c] (core) indicates the core structure of chlamydia oligosaccharides

EXAMPLE 2

Glycopeptides from hen egg ovalbumin were separated into fractions containing "complex-type" and "high mannose-type" carbohydrate using a ConA-Sepharose column (Krusius et al. (1976) *FEBS Lett.* 71:117–120). Briefly, 100 mg of ovalbumin was dissolved in 10 ml of 100 mM sodium bicarbonate buffer (buffer A), passed through a ConA-Sepharose column (5 ml) and washed with 10 column volumes of buffer A.

Ovalbumin containing a bi-antennary structure was eluted with 15 mM α-methyl-glucoside in buffer A (fraction 1) and that containing a "high mannose-type" structure was eluted with 200 mM α-methyl-mannoside in buffer A (fraction 2). Fractions 1 and 2 were dialyzed against distilled water, concentrated to a volume of 2 ml, to which 8 mg pronase B, 10 mM $CaCl_2$, 0.02% sodium azide in 0.1 M sodium borate buffer (pH 8.0) were added, and digested for 2 days. The digested material was evaporated to 1 ml and fractionated on a Sephadex G-50 column (1.5×50 cm). Sugar-containing fractions (monitored by phenol-sulfuric acid reaction) were collected and lyophilized.

Seven fluorescent-labeled oligosaccharide peaks were separated in two-dimensional sugar mapping. Three of the peaks present in fraction 2 from the ConA column were identified as "high mannose-type" (Peaks A to C in Table 5). Oligosaccharides present in fraction 2 from the ConA column were identified as "hybrid-type" or "complex-type" (peaks D to J in Table 5).

Fraction 2 of ovalbumin, which contained "high mannose-type" oligosaccharides (Table 5), inhibited infectivity (FIG. 2A). There was greater than 50% inhibition in inclusion counts from 25 to 6.25 µg/ml concentrations. In contrast, fraction 1, which contained oligosaccharides of the "complex-type" and "hybrid-type" (Table 5) had a lower rate of infectivity at the concentrations tested (FIG. 2B). The positive and negative controls with monoclonal antibodies reacted appropriately. All species of chlamydia, represented by $L_2$, AR-39 and 6BC strains, were inhibited equally by "high mannose-type" oligosaccharides.

"High mannose-type" glycopeptides inhibited attachment of live organisms effectively at 25–6.25 µg/ml concentrations, which paralleled the inhibition of infectivity (FIG. 3A). Attachment of formalin-fixed organisms also was inhibited by "high mannose-type" glycopeptides but to a greater degree [25–1.56 ug/ml (FIG. 3A)]. That may be due to the denaturation by formalin of proteinaceous ligands involved in attachment. The blocking of attachment of formalin-fixed organisms showed that inhibition was specific to the carbohydrate moiety. The fraction containing the "complex-type" oligosaccharides did not prevent attachment of either live or formalin-fixed organisms (FIG. 3B).

TABLE 5

| Peak | Code no.[a] | Percent | Structures |
|---|---|---|---|
| | | Fraction Containing the High Mannose Type | |
| A | M7.2 | 12.2 | Manα2Manα6\<br>            Manα6\<br>Manα3/     Manβ4GlcNAcβ4GlcNAc<br>Manα2Manα3/ |
| B | M6.1 | 55.9 | Manα6\<br>    Manα6\<br>Manα3/     Manβ4GlcNAcβ4GlcNAc<br>Manα2Manα3/ |
| C | M5.1 | 31.9 | Manα6\<br>    Manα6\<br>Manα3/     Manβ4GlcNAcβ4GlcNAc<br>Manα3/ |
| | | Fraction Containing the Complex Type | |

TABLE 5-continued

| Peak | Code no.[a] | Percent | Structures |
|---|---|---|---|
| D | H5.1 | 57.7 | Manα6\⟶Manα6\⟶GlcNAcβ4—Manβ4GlcNAcβ4GlcNAc / Manα3 / GlcNAcβ2 (Manα3 branch from upper Manα6) |
| H | H4.3 | 17.2 | Manα6, Manα3/GlcNAcβ4—Manβ4GlcNAcβ4GlcNAc, GlcNAcβ4\Manα3/GlcNAcβ2 |
| I | H4.4 | 21.8 | Manα6, Manα3/GlcNAcβ4—Manβ4GlcNAcβ4GlcNAc, Galβ4GlcNAcβ4\Manα3/GlcNAcβ2 |
| J | 301.1 | 3.3 | GlcNAcβ2Manα6\GlcNAcβ4—Manβ4GlcNAcβ4GlcNAc, GlcNAcβ4\Manα3/GlcNAcβ2 |

[a]Standards based on unit contribution (Takahashi & Tomiya (1992) supra)

It will be evident that various modifications can be made to the invention disclosed in the instant application without departing from the spirit thereof.

All references cited herein are herein incorporated by reference in entirety.

We claim:

1. A method of inhibiting binding of *Chlamydia* to mammalian cells comprising exposing said *Chlamydia*, said cells, or both, to an effective amount of a composition consisting essentially of high mannose type oligosaccharide; wherein said high mannose type oligosaccharide comprises at least five mannose residues, and comprises a trimannosyl core consisting of at least two mannosyl branches, one branch linked α1→6 and the other branch linked α1→3 to a mannose residue and having mannosyl substitution or branching at the α1→6Man residue of the trimannosyl core.

2. The method of claim 1, wherein said high mannose type oligosaccharide comprises at least three branches, each of said branches terminating in a mannose residue.

3. The method of claim 1, wherein said high mannose type oligosaccharide comprises at least four branches, each of said branches terminating in a mannose residue.

4. The method of claim 2, wherein the non-branched end of said high mannose type oligosacchande terminates in N-acetylglucosamine.

5. The method of claim 3, wherein the non-branched end of said high mannose type oligosaccharide terminates in N-acetylglucosamine.

6. The method of claim 4, wherein said terminal N-acetylglucosamine is one residue of chitobiose.

7. The method of claim 5, wherein said terminal N-acetylglucosamine is one residue of chitobiose.

8. The method of claim 6, wherein said chitobiose is linked to an asparagine.

9. The method of claim 7, wherein said chitobiose is linked to an asparagine.

10. The method of any one of claims 1–9 wherein said high mannose type oligosaccharide comprises at least six mannose residues.

11. The method of any one of claims 1–9, wherein said high mannose type oligosaccharide comprises at least seven mannose residues.

12. The method of any one of claims 1–9, wherein said high mannose type oligosaccharide comprises at least eight mannose residues.

13. The method of claim 1, wherein the mannose residues linked to the α1→6Man and α1→3Man branches of the trimannosyl core are α1→6Man, α1→2Man, and α1→3Man linkage forms in combination with optional α1→2Man substitution at non-reducing mannose residues.

14. The method of claim 13, wherein said high mannose type oligosaccharide comprises at least 8 mannose residues.

15. The method of claim 13, wherein said high mannose type oligosaccharide has the following structure:

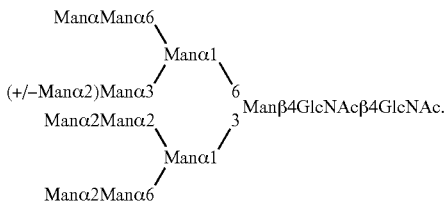

16. The method of claim 15, wherein said high mannose type oligosaccharide comprises 10 mannose residues.

17. The method of claim 15, wherein said high mannose type oligosaccharide comprises 11 mannose residues.

18. The method of claim 1, wherein said high mannose type oligosaccharide has a second α1→6Man and α1→3Man branch at the α1→6Man branch of the trimannosyl core, with optional α1→2Man substitution at non-reducing ends, and with α1→2Man substitution at the α1→3Man branch of the trimannosyl core.

19. The method of claim 18, wherein said high mannose type oligosaccharide has the following structure:

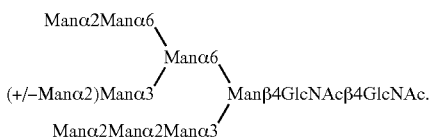

20. The method of claim 19, wherein said high mannose type oligosaccharide comprises 8 mannose residues.

21. The method of claim 19, wherein said high mannose type oligosaccharide comprises 9 mannose residues.

22. The method of claim 1, wherein said high mannose type oligosaccharide comprises a second α1→6Man and α1→3Man branch at the α1→6Man branch of the trimannosyl core, but without any α1→2Man substitution thereof, and with α1→2Man substitution at the α1→3Man branch of the trimannosyl core.

23. The method of claim 22, wherein said high mannose type oligosaccharide has the following structure:

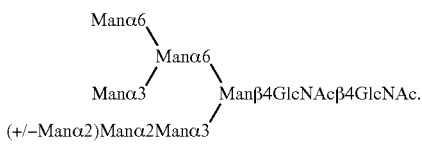

24. The method of claim 23, wherein said high mannose type oligosaccharide comprises 6 mannose residues.

25. The method of claim 23, wherein said high mannose type oligosaccharide comprises 7 mannose residues.

26. The method of claim 1, wherein said high mannose type oligosaccharide has a second α1→6Man and α1→3Man branch at the α1→6Man branch of the trimannosyl core, with optional α1→2Man substitution at non-reducing ends, and with α1→2Man substitution at the α1→3Man branch of the trimannosyl core, and further with optional peripheral α1→2Man substitutions.

27. The method of claim 26, wherein said high mannose type oligosaccharide has the following structure:

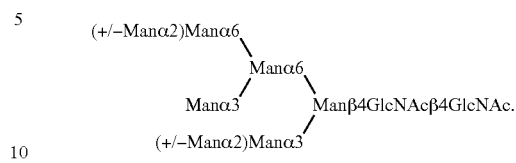

28. The method of claim 27, wherein said high mannose type oligosaccharide comprises 6 mannose residues.

29. The method of claim 27, wherein said high mannose type oligosaccharide comprises 7 mannose residues.

30. The method of claim 26, wherein said high mannose type oligosaccharide has the following structure:

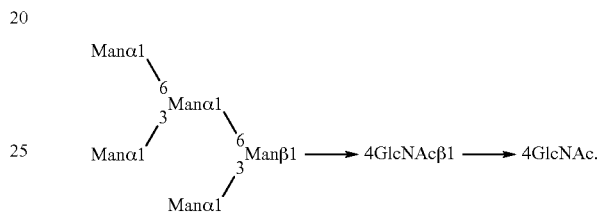

31. The method of claim 26, wherein said high mannose type oligosaccharide has the following structure:

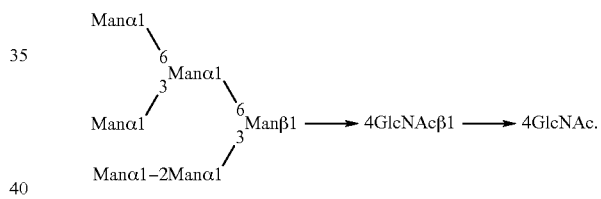

32. The method of claim 26, wherein said high mannose type oligosaccharide has the following structure:

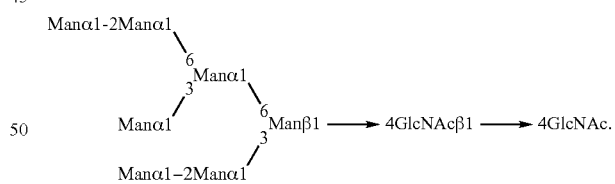

33. The method of claim 1, wherein said high mannose type oligosacchande is derived from the major outer membrane protein of *Chlamydia*.

34. The method of claim 1, wherein said high mannose type oligosaceharide is derived from hen egg ovalbumin.

35. The method of claim 34, wherein said oligosaccharide derived from hen egg ovalbumin is modified by the addition of additional mannose residues to one or more of the mannosyl branches.

36. The method of claim 1, wherein said high mannose type oligosaccharide is synthesized either chemically and/or enzymatically.

37. The method of claim 36, wherein said synthetic high mannose type oligosaccharide has the following structure:

$$\begin{array}{c}
\text{Man}\alpha 2\text{Man}\alpha 6 \\
\diagdown \\
\text{Man}\alpha 6 \\
\diagup \quad \diagdown \\
(+/-\text{Man}\alpha 2)\text{Man}\alpha 3 \qquad \text{Man}\beta 4\text{GlcNAc}\beta 4\text{GlcNAc.} \\
\diagup \\
\text{Man}\alpha 2\text{Man}\alpha 2\text{Man}\alpha 3
\end{array}$$

38. The method of claim 1, wherein said high mannose type oligosaccharide has been modified to contain greater than three mannosyl branches.

39. A method of inhibiting binding of *Chlamydia* to mammalian cells comprising exposing said *Chlamydia*, said cells, or both, to an effective amount of a composition consisting of high mannose type oligosaccharide and one or more of an excipient, a diluent, and/or a filler; wherein said high mannose type oligosaccharide comprises at least five mannose residues, and comprises a trimannosyl core consisting of at least two mannosyl branches, one branch linked α1→6 and the other branch linked α1→3 to a mannose residue and having mannosyl substitution or branching at the α1→6Man residue of the trimannosyl core.

40. The method of claim 39, wherein said high mannose type oligosaccharide comprises at least three branches, each of said branches terminating in a mannose residue.

41. The method of claim 39, wherein said high mannose type oligosaccharide comprises at least four branches, each of said branches terminating in a mannose residue.

42. The method of claim 40, wherein the non-branched end of said high mannose type oligosaccharide terminates in N-acetylglucosamine.

43. The method of claim 41, wherein the non-branched end of said high mannose type oligosaccharide terminates in N-acetylglucosamine.

44. The method of claim 42, wherein said terminal N-acetylglucosamine is one residue of chitobiose.

45. The method of claim 43, wherein said terminal N-acetylglucosamine is one residue of chitobiose.

46. The method of claim 44, wherein said chitobiose is linked to an asparagine.

47. The method of claim 45, wherein said chitobiose is linked to an asparagine.

48. The method of any one of claims 39–47, wherein said high mannose type oligosaccharide comprises at least six mannose residues.

49. The method of any one of claims 39–47, wherein said high mannose type oligosaccharide comprises at least seven mannose residues.

50. The method of any one of claims 39–47, wherein said high mannose type oligosaccharide comprises at least eight mannose residues.

51. The method of claim 39, wherein the mannose residues linked to the α1→6Man and α1→3Man branches of the trimannosyl core are α1→6Man, α1→2Man, and α1→3Man linkage forms in combination with optional α1→2Man substitution at non-reducing mannose residues.

52. The method of claim 51, wherein said high mannose type oligosaccharide comprises at least eight mannose residues.

53. The method of claim 51, wherein said high mannose type oligosaccharide has the following structure:

$$\begin{array}{c}
\text{Man}\alpha\text{Man}\alpha 6 \\
\diagdown \\
\text{Man}\alpha 1 \\
\diagup \quad \diagdown \\
(+/-\text{Man}\alpha 2)\text{Man}\alpha 3 \qquad 6 \\
\diagup \qquad \qquad \text{Man}\beta 4\text{GlcNAc}\beta 4\text{GlcNAc.} \\
\text{Man}\alpha 2\text{Man}\alpha 2 \qquad 3 \\
\diagdown \quad \diagup \\
\text{Man}\alpha 1 \\
\diagup \\
\text{Man}\alpha 2\text{Man}\alpha 6
\end{array}$$

54. The method of claim 53, wherein said high mannose type oligosaccharide comprises ten mannose residues.

55. The method of claim 53, wherein said high mannose type oligosaceharide comprises eleven mannose residues.

56. The method of claim 39, wherein said high mannose type oligosaccharide has a second α1→6Man and α1→3Man branch at the α1→6Man branch of the trimannosyl core, with optional α1→2Man substitution at non-reducing ends, and with α1→2Man substitution at the α1→3Man branch of the trimannosyl core.

57. The method of claim 56, wherein said high mannose type oligosaccharide has the following structure:

$$\begin{array}{c}
\text{Man}\alpha 2\text{Man}\alpha 6 \\
\diagdown \\
\text{Man}\alpha 6 \\
\diagup \quad \diagdown \\
(+/-\text{Man}\alpha 2)\text{Man}\alpha 3 \qquad \text{Man}\beta 4\text{GlcNAc}\beta 4\text{GlcNAc.} \\
\diagup \\
\text{Man}\alpha 2\text{Man}\alpha 2\text{Man}\alpha 3
\end{array}$$

58. The method of claim 57, wherein said high mannose type oligosaccharide comprises eight mannose residues.

59. The method of claim 57, wherein said high mannose type oligosaccharide comprises nine mannose residues.

60. The method of claim 39, wherein said high mannose type oligosaccharide comprises a second α1→6Man and α1→3Man branch at the α1→6Man branch of the trimannosyl core, but without any α1→2Man substitution thereof, and with α1→2Man substitution at the α1→3Man branch of the trimannosyl core.

61. The method of claim 60, wherein said high mannose type oligosaccharide has the following structure:

$$\begin{array}{c}
\text{Man}\alpha 6 \\
\diagdown \\
\text{Man}\alpha 6 \\
\diagup \quad \diagdown \\
\text{Man}\alpha 3 \qquad \text{Man}\beta 4\text{GlcNAc}\beta 4\text{GlcNAc.} \\
\diagup \\
(+/-\text{Man}\alpha 2)\text{Man}\alpha 2\text{Man}\alpha 3
\end{array}$$

62. The method of claim 61, wherein said high mannose type oligosaccharide comprises six mannose residues.

63. The method of claim 61, wherein said high mannose type oligosaccharide comprises seven mannose residues.

64. The method of claim 39, wherein said high mannose type oligosaccharide has a second α1→6Man and α1→3Man branch at the α1→6Man branch of the trimannosyl core, with optional α1→2Man substitution at non-reducing ends, and with α1→2Man substitution at the α1→3Man branch of the trimannosyl core, and further with optional peripheral α1→2Man substitutions.

65. The method of claim 64, wherein said high mannose type oligosaccharide has the following structure:

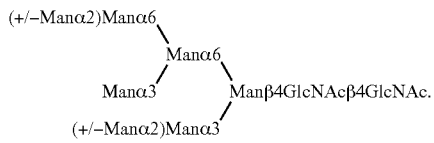

66. The method of claim 65, wherein said high mannose type oligosaccharide comprises six mannose residues.

67. The method of claim 65, wherein said high mannose type oligosaccharide comprises seven mannose residues.

68. The method of claim 64, wherein said high mannose type oligosaccharide has the following structure:

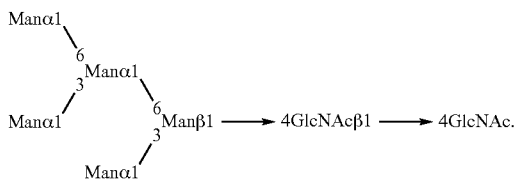

69. The method of claim 64, wherein said high mannose type oligosaccharide has the following structure:

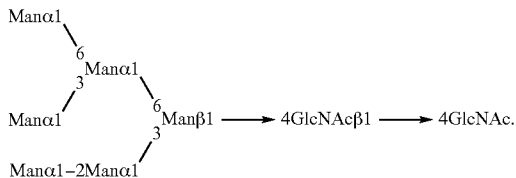

70. The method of claim 64, wherein said high mannose type oligosaccharide has the following structure:

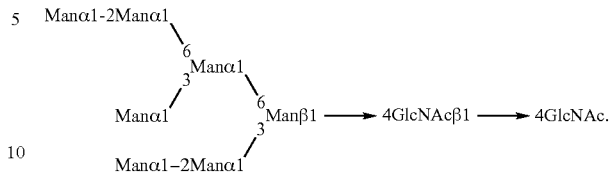

71. The method of claim 39, wherein said high mannose type oligosaccharide is derived from the major outer membrane protein of *Chlamydia*.

72. The method of claim 39, wherein said high mannose type oligosaccharide is derived from hen egg ovalbumin.

73. The method of claim 72, wherein said oligosaccharide derived from hen egg ovalbumin is modified by the addition of additional mannose residues to one or more of the mannosyl branches.

74. The method of claim 39, wherein said high mannose type oligosaccharide is synthesized either chemically and/or enzymatically.

75. The method of claim 74, wherein said synthetic high mannose type oligosaccharide has the following structure:

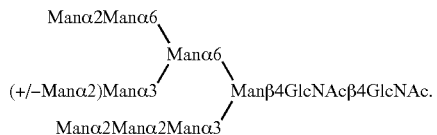

76. The method of claim 39, wherein said high mannose type oligosacchande has been modified to contain greater than three mannosyl branches.

* * * * *